(12) United States Patent
Georgi et al.

(10) Patent No.: US 10,845,292 B2
(45) Date of Patent: Nov. 24, 2020

(54) METHOD FOR CORRECTING LOW PERMEABILITY LABORATORY MEASUREMENTS FOR LEAKS

(71) Applicant: Saudi Arabian Oil Company, Dhahran (SA)

(72) Inventors: Daniel T. Georgi, Houston, TX (US); Huangye Chen, Cypress, TX (US); Hui-Hai Liu, Katy, TX (US)

(73) Assignee: Saudi Arabian Oil Company, Dhahran (SA)

( * ) Notice: Subject to any disclaimer, the term of this patent is extended or adjusted under 35 U.S.C. 154(b) by 238 days.

(21) Appl. No.: 16/000,651

(22) Filed: Jun. 5, 2018

(65) Prior Publication Data

US 2018/0364142 A1 Dec. 20, 2018

Related U.S. Application Data

(60) Provisional application No. 62/521,786, filed on Jun. 19, 2017.

(51) Int. Cl.
*G01N 15/08* (2006.01)
*E21B 49/08* (2006.01)
*G01N 33/24* (2006.01)

(52) U.S. Cl.
CPC ....... *G01N 15/0826* (2013.01); *E21B 49/088* (2013.01); *G01N 15/0806* (2013.01); *G01N 33/241* (2013.01)

(58) Field of Classification Search
CPC .. G01N 15/08; G01N 15/0806; G01N 15/082; G01N 15/0826; E21B 49/005; E21B 49/02; E21B 49/087; E21B 49/088; G01M 3/02; G01M 3/26

USPC ....... 73/38, 40, 49.2, 152.05, 152.07, 152.11
See application file for complete search history.

(56) References Cited

U.S. PATENT DOCUMENTS

| | | | | |
|---|---|---|---|---|
| 4,389,878 A | * | 6/1983 | Manzie, Jr. | ........ G01N 15/0826 73/38 |
| 2018/0348111 A1 | * | 12/2018 | Hannon | ............. G01N 15/0806 |

OTHER PUBLICATIONS

Alnoaimi and Kovscek, "Experimental and Numerical Analysis of Gas Transport in Shale including the Role of Sorption," Paper SPE 166375, presented at the SPE Annual Technical Conference and Exhibition, Sep. 30-Oct. 2, 2013, 16 pages.
An et al., "A new study of magnetic nanoparticle transport and quantifying magnetization analysis in fractured shale reservoir using numerical modeling," Journal of Natural Gas Science and Engineering, vol. 28, Jan. 2016, 21 pages.

(Continued)

*Primary Examiner* — Benjamin R Schmitt
(74) *Attorney, Agent, or Firm* — Fish & Richardson P.C.

(57) ABSTRACT

A method for correcting low permeability laboratory measurements for leaks. A pulse-decay permeability (PDP) experiment is performed on a core sample retrieved from a formation. The PDP experiment includes flowing fluid through the core sample in a sealed enclosure. In response to flowing the fluid through the core sample, a change in fluid pressure is measured over time. Based on the change in fluid pressure over time, a leakage of fluid from the sealed enclosure is determined. In response to determining the leakage of fluid from the sealed enclosure, an analytical model of the leakage is determined based on the change in fluid pressure over time.

11 Claims, 16 Drawing Sheets

(56) References Cited

OTHER PUBLICATIONS

Cronin, "Core-scale heterogeneity and dual-permeability pore structures in the Barnett Shale," Thesis for Degree of Master of Science in Geological Sciences at the University of Texas at Austin, Dec. 2014, 174 pages.
Darabi et al., "Gas flow in ultra-tight shale strata," Journal of Fluid Mechanics, vol. 710, Nov. 10, 2012, 20 pages.
Finsterle and Persoff, "Determining permeability of tight rock samples using inverse modeling," Water Resources Research, vol. 33, No. 8, Aug. 1997, 9 pages.
Heller et al., "Experimental investigation of matric permeability of gas shale," AAPG Bulletin, vol. 98, No. 5, May 2014, 21 pages.
Warren and Root, "The behavior of naturally fractured reservoirs," SPE-426-PA, SPE Journal, vol. 3, No. 3, Sep. 1963, 11 pages.
Yan et al., "General multi-porosity simulation for fractured reservoir modeling," Journal of Natural Gas Science Engineering, vol. 33, Jul. 2016, 16 pages.
Bourbie and Walls, "Pulse decay permeability: analytical solution and experimental test," SPE Journal, vol. 22, No. 5, Oct. 1982, 11 pages.
Brace et al., "Permeability of granite under high pressure," Journal of Geophysics Res. vol. 73, No. 6, Mar. 15, 1968, 12 pages.
Brezovski and Cui, "Laboratory permeability measurements of unconventional reservoirs: useless or full of information? A montney example from the western Canadian sedimentary basin," Society of Petroleum Engineers, presented at the SPE Unconventional Resources Conference and Exhibition—Asia Pacific, Nov. 11-13, 2013, 12 pages.
Cui et al., "Measurements of gas permeability and diffusivity of tight reservoir rocks: different approaches and their applications," Geofluids, vol. 9, No. 3, Aug. 2009, presented at the AAPG Convention, Jun. 7-10, 2009, 18 pages.
Dicker and Smits, "A practical approach for determining permeability from laboratory pressure-pulse decay measurements," SPE-17578, Society of Petroleum Engineers, Nov. 1-4, 1988, 8 pages.
Egermann et al., "A fast and direct method of permeability measurements on drill cuttings," Society of Petroleum Engineers, SPE Reservoir Evaluation and Engineering, vol. 8, No. 4, Aug. 2005, 7 pages.
Jones, "A Technique for Faster Pulse-Decay Permeability Measurements in Tight Rocks," presented at the 1994 SPE Annual Technical Conference and Exhibition, Sep. 25-28, 1994, SPE Formation Evaluation, Mar. 1997, 7 pages.
Luffel et al., "Matrix permeability measurement of gas productive shales," SPE-26633-MS, Society of Petroleum Engineers, SPE Annual Technical Conference and Exhibition, Oct. 3-6, 1993, 10 pages.
Ning et al., "The measurement of Matrix and Fracture Properties in Naturally Fractured Cores," SPE-25898, Society of Petroleum Engineers, Low Permeability Reservoirs Symposium, Apr. 26-28, 1993, 15 pages.
ResTech, "Development of laboratory and petrophysical techniques for evaluating shale reservoirs," GRI-95/0496, Gas Research Institute, Apr. 1996, 306 pages.
Thomas et al., "Fractured reservoir simulation," SPE-9305-PA, SPE Journal, vol. 23, No. 1, Feb. 1983, 13 pages.
Trimmer et al., "Effect of pressure and stress on the water transport in intact and fractured gabbro and granite," Journal of Geophysical Research, vol. 85, Dec. 10, 1980, 13 pages.
Yamada and Jones, "A review of pulse technique for permeability measurements," SPE Journal, vol. 20, No. 5, Oct. 1980, 2 pages.
Gulf Cooperation Council Examination Report issued in GCC Application No. 2018-35502 dated Dec. 10, 2019, 4 pages.
International Search Report issued in International Application No. PCT/US2018/037231 dated Sep. 14, 2018, 18 pages.
Gulf Cooperation Council Examination Report issued in GCC Application No. 2018-35502 dated Apr. 11, 2020, 4 pages.

* cited by examiner

METHOD FOR CORRECTING LOW PERMEABILITY LABORATORY MEASUREMENTS FOR LEAKS

CROSS-REFERENCE TO RELATED APPLICATION(S)

This application claims the benefit of priority to U.S. Provisional Patent Application No. 62/521,786, filed Jun. 19, 2017 and entitled "METHOD FOR CORRECTING LOW PERMEABILITY LABORATORY MEASUREMENTS FOR LEAKS", the contents of which are hereby incorporated by reference.

TECHNICAL FIELD

This specification relates to measuring permeability of low permeability rock formations.

BACKGROUND

Tight rock formations such as shales have attracted increased attention as potential hydrocarbon resources due to the development of technology like hydraulic fracturing and horizontal drilling, which has allowed production from these unconventional resources to become economically viable. The permeability of such rock formations is a parameter to characterize the reservoir, and is used to predict a reservoir's productivity and profitability. Accurately measuring the permeability of such unconventional resources is useful in determining the ability to produce from a reservoir.

SUMMARY

This specification describes technologies relating to correcting low permeability laboratory measurements for leaks.

Certain aspects of the subject matter described here can be implemented as a method. A pulse-decay permeability (PDP) experiment is performed on a core sample retrieved from a formation. The PDP experiment includes flowing fluid through the core sample in a sealed enclosure. In response to flowing the fluid through the core sample, a change in fluid pressure is measured over time. Based on the change in fluid pressure over time, a leakage of fluid from the sealed enclosure is determined. In response to determining the leakage of fluid from the sealed enclosure, an analytical model of the leakage is determined based on the change in fluid pressure over time.

This, and other aspects, can include one or more of the following features.

Based on the change in fluid pressure over time and on the analytical model of the leakage, a permeability model representing a permeability of the core sample can be determined.

The permeability can be determined by fitting the non-straight curve with consideration of the leakage effect.

The sealed enclosure can include an upstream reservoir, a downstream reservoir, and a core holder between the upstream reservoir and the downstream reservoir. Performing the PDP experiment on the core sample can include positioning the core sample in the core holder, flowing the fluid into the upstream reservoir, flowing the fluid through the core sample in the core holder, and flowing the fluid into the downstream reservoir. The leakage of fluid from the upstream and downstream reservoirs can be determined based on the pressure difference between an upstream reservoir and a downstream reservoir.

The core sample can be an unfractured core sample.

In response to flowing the fluid through the unfractured core sample, measuring the change in fluid pressure over time can include recording pressure transient curves for each of the upstream and downstream reservoirs.

A log of an experimental pressure difference between the upstream and downstream reservoirs can be determined based on the pressure transient curves.

Determining the leakage of the fluid based on the change in fluid pressure over time can include determining that the log of the experimental pressure difference is substantially a straight line and determining an absence of the leakage from the upstream and downstream reservoirs.

Determining the leakage of the fluid based on the change in fluid pressure over time can include determining that the log of the experimental pressure difference is substantially a non-straight curve and determining a presence of leakage from the sealed enclosure.

In response to determining the leakage of fluid from the upstream and downstream reservoirs, the leakage rate can be determined based on the change in fluid pressure over time by determining a theoretical pressure difference between the upstream and downstream reservoirs based on parameters of the fluid flowed through the unfractured core sample, where the theoretical pressure difference can be independent of the leakage from the sealed enclosure. In response to determining the leakage of fluid from the sealed enclosure, the leakage rate can be determined based on the change in fluid pressure over time by comparing the theoretical pressure difference and the experimental pressure difference.

The core sample can be a fractured core sample including a fracture formed in a matrix of the core sample.

In response to flowing the fluid through the fractured core sample, measuring the change in fluid pressure over time can include measuring a first-stage change in fluid pressure over time, where the first-stage change in fluid pressure can be based on flow of the fluid through the fracture. In response to flowing the fluid through the core sample, measuring the change in fluid pressure over time can include measuring a second-stage change in fluid pressure over time, where the second-stage change in fluid pressure can be based on flow of the fluid through the matrix after the flow of the fluid through the fracture. Based on the change in fluid pressure over time, determining the leakage of fluid from the sealed enclosure can include determining that a log of the second-stage change in fluid pressure over time deviates from a substantially straight line.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a method for correcting low and ultralow transient permeability measurements for instrument leaks during a core permeability experiment utilizing gas as the fluid medium (for example, helium or nitrogen). The method is applicable to single and dual permeability systems, corresponding to one- and two-stage pulse-decay permeability (PDP) experiments, respectively. The first derivative (that is, slope) of the log of the pressure difference (between the upstream and downstream reservoirs) curve is calculated and plotted versus time. If this derivative line diverges from a constant-derivative line with time, there exists gas leak in the measurement system. Based on this divergence, the leakage rate can be simultaneously calculated and compensated for, in order to estimate the permeability of the sample more accurately.

The pulse-decay permeability (PDP) method takes relatively less time to measure permeability in comparison to steady-state permeability methods, especially for tight, low permeability rock formations. The PDP method preserves the structure of the rock sample in contrast to crushed sample experiments, and it can also reflect anisotropic properties (for example, horizontal and vertical permeability) of a rock formation by using core samples with different orientations. The method described in this specification can be implemented, so as to realize one or more of the following advantages. Permeability measurements can be corrected for leakage, if any leakage is present in the testing apparatus, thereby avoiding a potential need to rerun experiments. Because the structure of the rock sample is preserved, the method can be applicable to single and dual permeability systems, accurately measuring permeability by correcting for any potential leakage at each stage of the experiment.

Figure 1:
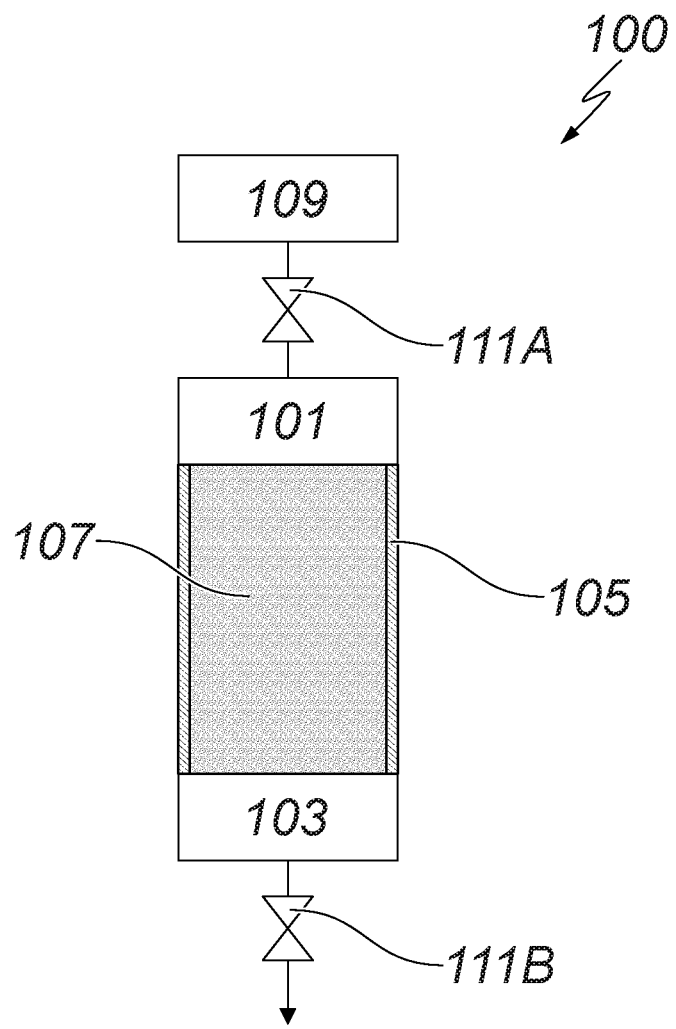
FIG. 1 is a schematic diagram of an example core sample prepared for a pulse-decay permeability (PDP) experiment.

FIG. 1 shows a schematic diagram for an example PDP experiment. The system 100 includes an upstream reservoir 101, a downstream reservoir 103, and a core holder 105. A core sample 107 is placed in the core holder 105, which can hold a high hydrostatic confining pressure-usually around 2,000 to 5,000 pounds per square inch gauge (psig)—and then a test gas (for example, helium or nitrogen) can be pumped into upstream reservoir 101 and downstream reservoir 105 for enough time to ensure the upstream pressure, downstream pressure, and pore pressure reach equilibrium—usually around 1,000 to 2,000 psig. The high pressure can lessen the Klinkenberg slipping effect during gas transport.

The upstream reservoir 101 is provided a pulse pressure that is a small percentage of the initial gas pressure (for example, an additional 4% of initial 1,000 psi, or 40 psi) by pressure source 109. Due to the pulse pressure, the test gas flows from the upstream reservoir 101 to the downstream reservoir 103 by passing through the core sample 107. The pressures in the upstream reservoir 101 and downstream reservoir 103 are recorded as a function of time, and the permeability of the core sample 107 is estimated by the changes of pressures in the reservoirs.

Figure 2B:
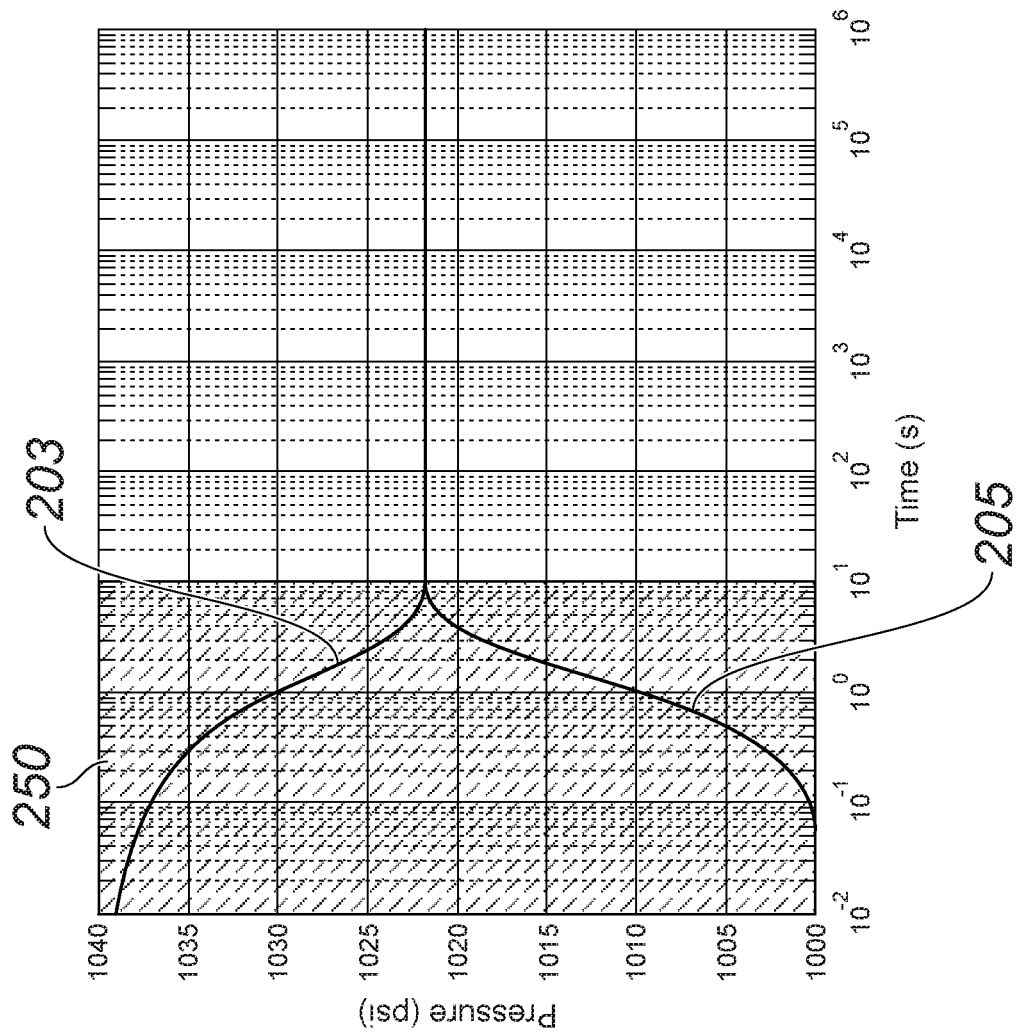
FIGS. 2A, 2B, 2C, and 2D are simplified diagrams and pressure graphs of example PDP experiments.
Figure 2A:
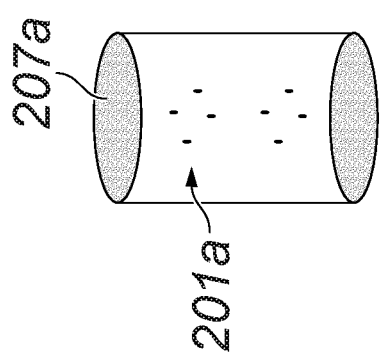

Unfractured core samples can be described as single permeability systems, which are characterized by matrix permeability. FIG. 2A shows a single permeability system of matrix 201A, and FIG. 2B shows the corresponding pressure transient curves for the upstream reservoir 101 (curve 203) and downstream reservoir 103 (curve 205). For the graph shown in FIG. 2B, the x-axis is time in seconds (s), and the y-axis is pressure in pounds per square inch (psi). Due to the gas flow through the core sample 207A, the pressure of the upstream reservoir 101 declines while the pressure of the downstream reservoir 103 increases until the reservoirs reach equilibrium (that is, the pressure difference between the reservoirs becomes zero). This process is referred as the first-stage process 250.

Figure 2D:
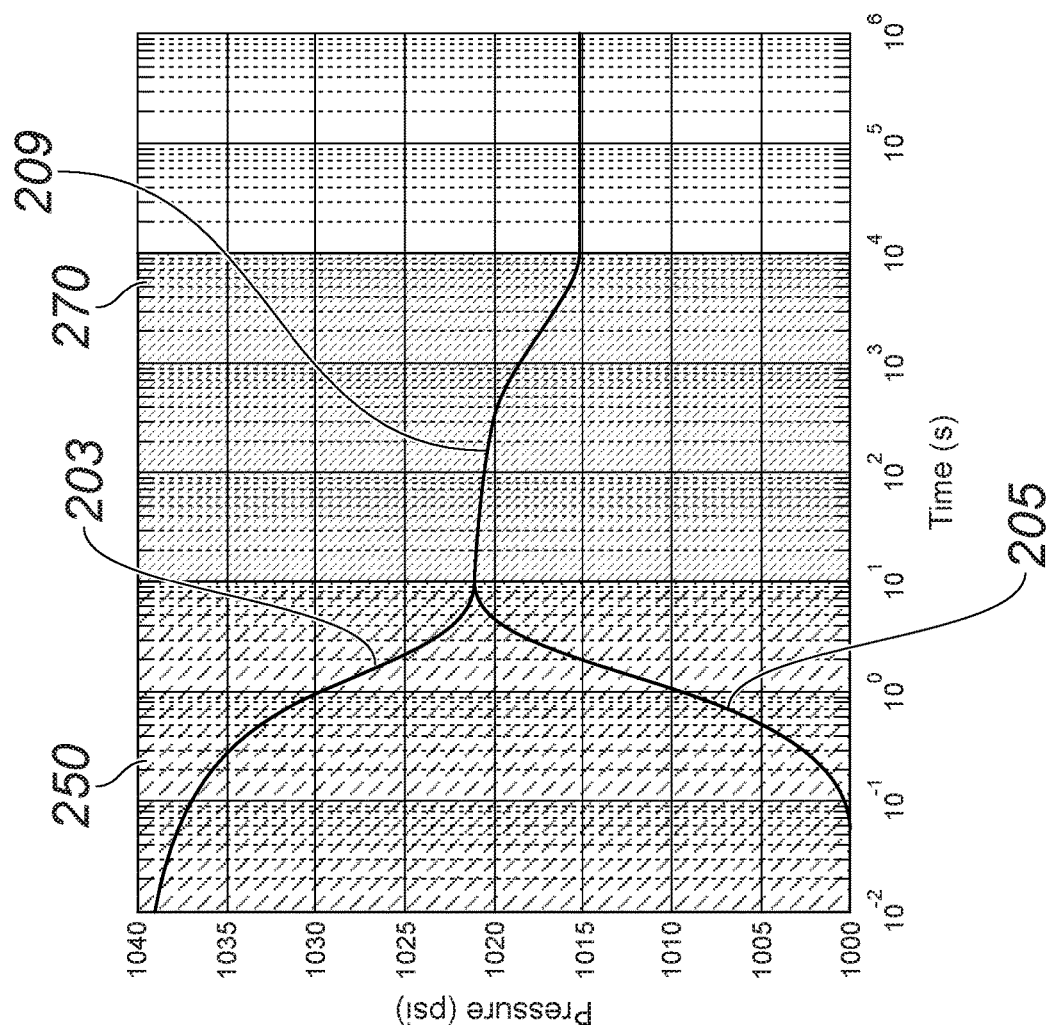
Figure 2C:
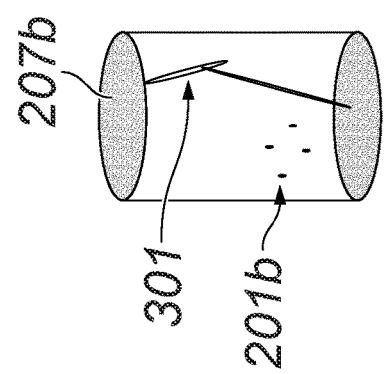

If a rock formation is fractured, its permeability can be characterized by fracture permeability, in addition to matrix permeability. Such fractured core samples are described as dual-permeability systems because the system includes two continua and connected transport structures with different permeability values. FIG. 2C shows a dual-permeability system of matrix 201B and fracture 301, and FIG. 2D shows the corresponding pressure transient curves. For the graph shown in FIG. 2D, the x-axis is time in s, and the y-axis is pressure in psi. As shown in FIG. 2D, the pressure transient curves of a dual permeability system have a second decline 209 after the first-stage process 250. The first-stage process 250 is generally attributed to the core fracture 301. The second decline 209 is attributed to the smaller permeability of the core matrix 201B and is referred as the second-stage process 270.

Apparatus leakage is a potential source of error in measuring permeability, and any leakage can have a significant impact on the measurement, especially for tight rock formations like shales which have very low permeability. Therefore, it can be useful to correct permeability assessments of low permeability samples by taking into account any fluid leakage in the measurement system.

Figure 3A:
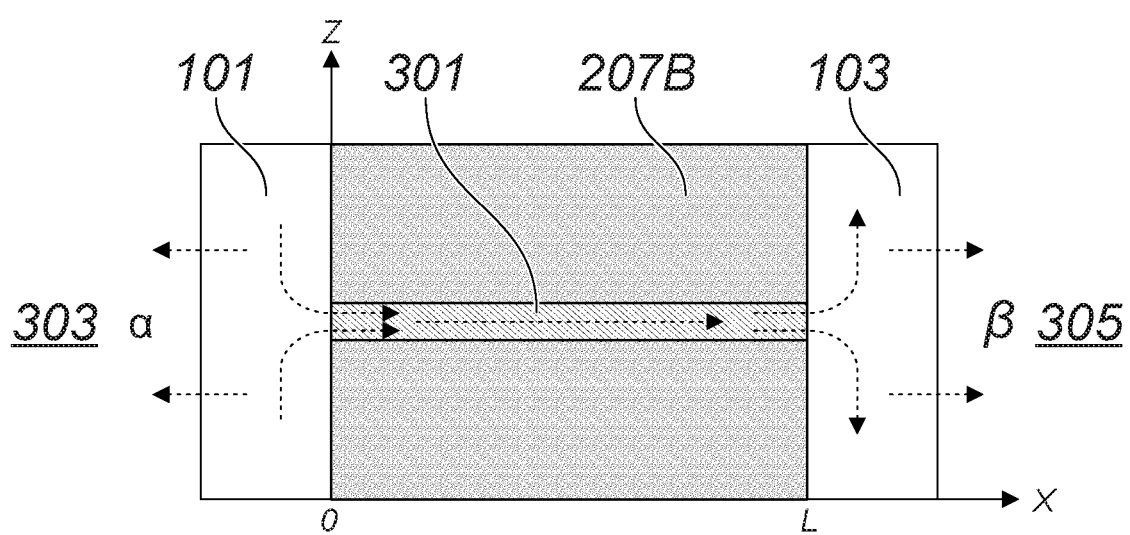
FIGS. 3A and 3B are simplified flow graphs of example 1st-stage PDP experiments.

FIG. 3A shows the gas flow for a fractured core sample 207B during the first-stage process 250 with gas leakage. After the pressure source 109 provides the pulse pressure to the upstream reservoir 101, the gas flows from the upstream reservoir 101 into the core fracture 301 and then into the downstream reservoir 103. During this first-stage process 250, the gas also penetrates the matrix pores of the core sample 207B. Because the fracture permeability is much larger than the matrix permeability (usually by orders of magnitude), the impact of the matrix permeability is negligible during the first-stage process 250. Leakage rate is defined as the rate of pressure decrease with time due to leakage in psi/s, and the leakage rates are identified as α 303 and β 305 for the upstream reservoir 101 and the downstream reservoir 103, respectively.

In the first-stage process 250 of a PDP experiment, the upstream and downstream pressures are recorded simultaneously. The transient pressure of the system can be modelled mathematically, and the analytical solution for the model can be used to determine core sample characteristics. Using Darcy's equation and the mass conservation equation, the pressure inside the sample, P(x,t), as a function of the distance x along the sample and time t can be solved using the following differential equation:

$$\frac{\partial^2 P(x, t)}{\partial x^2} = \frac{c\mu\phi_f}{k_f} \frac{\partial P(x, t)}{\partial t}, 0 < x < L, t > 0 \tag{1}$$

$$P(x, 0) = P_2(0), 0 < x < L, \tag{2}$$

$$P(0, t) = P_1(t), t \geq 0, \tag{3}$$

-continued $$P(L, t) = P_2(t), t \geq 0, \quad (4)$$

where $P_1$, $P_2$, $k_f$, $c$, $\mu$, $\phi_f$, and $L$ are the upstream reservoir 101 pressure, the downstream reservoir 103 pressure, the fracture permeability, the gas compressibility, the gas viscosity, the fracture porosity, and the length of the core sample 107, respectively.

Gas leakage may exist in the testing apparatus, and the mass conservation equation at the upper and bottom faces of the core sample 107 are:

$$\frac{\partial P_1}{\partial t} = \frac{k_f}{c\mu\phi_f L} \frac{V_f}{V_1} \frac{\partial P(x,t)}{\partial x} + \alpha, t > 0, x = 0, \quad (5)$$

$$\frac{\partial P_2}{\partial t} = -\frac{k_f}{c\mu\phi_f L} \frac{V_f}{V_1} \frac{\partial P(x,t)}{\partial x} + \beta, t > 0, x = L, \quad (6)$$

where $V_1$, $V_2$, $V_f$, $\alpha$, and $\beta$ are the upstream reservoir volume, the downstream reservoir volume, the fracture volume, the upstream leakage rate, and the downstream leakage rate, respectively.

Some dimensionless parameters are defined to simplify the equations. Dimensionless time ($t_D$) and distance ($x_D$) are defined by Eq. 7.

$$t_D = \frac{k_f}{c\mu\phi_f L^2} t, x_D = \frac{x}{L} \quad (7)$$

The dimensionless parameters a and b are defined by Eq. 8.

$$a = \frac{V_f}{V_1}, b = \frac{V_f}{V_2} \quad (8)$$

The dimensionless gas leakage rates of upstream reservoir 101 and downstream reservoir 103 are defined by Eqs. 9-10.

$$\alpha_{D0} = \frac{c\mu\phi_f L^2}{k_f} \frac{1}{P_1(0) - P_2(0)} \alpha, \quad (9)$$

$$\beta_{D0} = \frac{c\mu\phi_f L^2}{k_f} \frac{1}{P_1(0) - P_2(0)} \beta \quad (10)$$

The normalized pressures of the core sample 107 ($P_D$), the upstream reservoir 101 ($P_{D1}$), and the downstream reservoir 103 ($P_{D2}$) are:

$$P_D(x_D, t_D) = \frac{P(x,t) - P_2(0)}{P_1(0) - P_2(0)}, \quad (11)$$

$$P_{D1}(t_D) = \frac{P_1(t) - P_2(0)}{P_1(0) - P_2(0)}, \quad (12)$$

$$P_{D2}(t_D) = \frac{P_2(t) - P_2(0)}{P_1(0) - P_2(0)}, \quad (13)$$

where $P_2(0)$ is the initial gas pressure in the PDP system 100, and $P_1(0)$ is the initial gas pressure plus the increased pressure in the upstream reservoir 101 before gas flow occurs.

With the dimensionless parameters, the differential equations can be converted to:

$$\frac{\partial^2 P_D(x_D, t_D)}{\partial x_D^2} = \frac{\partial P_D(x_D, t_D)}{\partial t_D}, 0 < x_D < 1, t_D > 0, \quad (14)$$

with the initial boundary conditions:

$$P_D(x_D, 0) = 0, 0 < x_D < 1, \quad (15)$$

$$P_D(0, t_D) = P_{D1}(t_D), t_D \geq 0, \quad (16)$$

$$P_D(1, t_D) = P_{D2}(t_D), t_D \geq 0, \quad (17)$$

$$\frac{\partial P_{D1}(t_D)}{\partial t_D} = a\frac{\partial P_D(x_D, t_D)}{\partial x} + \alpha_{D0}, t_D \geq 0, x_D = 0, \quad (18)$$

$$\frac{\partial P_{D2}(t_D)}{\partial t_D} = -b\frac{\partial P_D(x_D, t_D)}{\partial x_D} + \beta_{D0}, t_D \geq 0, x_D = 1. \quad (19)$$

Through Laplace transform and inverse Laplace transform, the normalized upstream and downstream pressure with gas leakage are the following:

$$P_{D1}(t_D) = \frac{P_1(t) - P_2(0)}{P_1(0) - P_2(0)} = \quad (20)$$

$$C_1 + 2\sum_{n=1}^{\infty} e^{(-t_D\theta_n^2)} \frac{(ab^2 + a\theta_n^2)\left(1 - \frac{\alpha_{D0}}{\theta_n^2}\right) + \frac{a^2b - a\theta_n^2}{\theta_n^2 \cos(\theta_n)}\beta_{D0}}{\theta_n^4 + \theta_n^2(a + a^2 + b + b^2) + ab(a + b + ab)} +$$

$$\frac{b\alpha_{D0}}{a+b+ab}t_D + \frac{a\beta_{D0}}{a+b+ab}t_D,$$

$$P_{D2}(t_D) = \frac{P_2(t) - P_2(0)}{P_1(0) - P_2(0)} = \quad (21)$$

$$C_2 + 2\sum_{n=1}^{\infty} e^{(-t_D\theta_n^2)} \frac{\frac{ab^2 - b\theta_n^2}{\cos(\theta_n)}\left(1 - \frac{\alpha_{D0}}{\theta_n^2}\right) + \frac{a^2b + a\theta_n^2}{q^2}\beta_{D0}}{\theta_n^4 + \theta_n^2(a + a^2 + b + b^2) + ab(a + b + ab)} +$$

$$\frac{b\alpha_{D0}}{a+b+ab}t_D + \frac{a\beta_{D0}}{a+b+ab}t_D,$$

where $C_1$ and $C_2$ are constants calculated by:

$$C_1 = 1 - 2\sum_{n=1}^{\infty} \frac{(ab^2 + a\theta_n^2)\left(1 - \frac{\alpha_{D0}}{\theta_n^2}\right) + \frac{a^2b - a\theta_n^2}{\theta_n^2 \cos(\theta_n)}\beta_{D0}}{\theta_n^4 + \theta_n^2(a + a^2 + b + b^2) + ab(a + b + ab)}, \quad (22)$$

$$C_2 = -2\sum_{n=1}^{\infty} \frac{\frac{ab^2 + b\theta_n^2}{\cos(\theta_n)}\left(1 - \frac{\alpha_{D0}}{\theta_n^2}\right) + \frac{a^2b + a\theta_n^2}{q^2}\beta_{D0}}{\theta_n^4 + \theta_n^2(a + a^2 + b + b^2) + ab(a + b + ab)}, \quad (23)$$

where $\theta_n$ are the roots of the following equation:

$$\tan(\theta_n) = \frac{(a+b)\theta_n}{\theta_n^2 - ab}, \theta_n > 0. \quad (24)$$

Figure 3B:
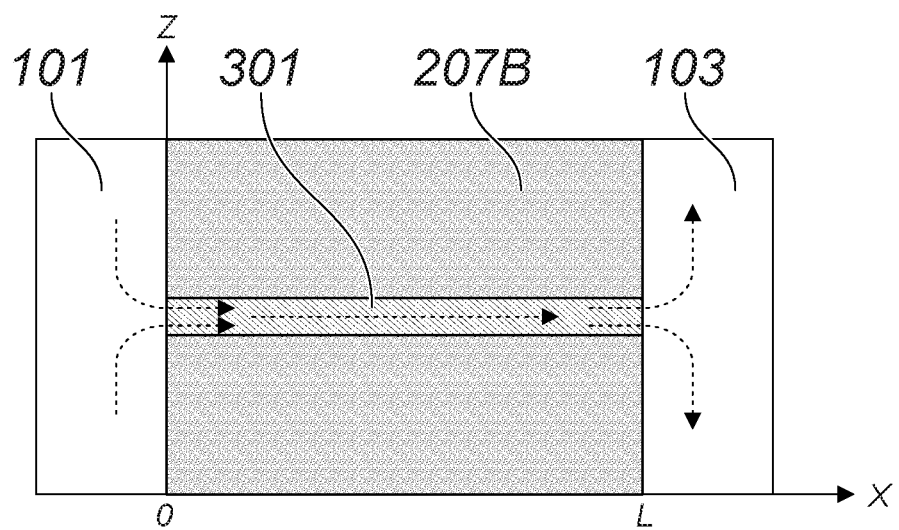

The leakage rates $\alpha$ 303 or $\beta$ 305 (or even both) can be zero for no gas leakage conditions and can be attributed to gas desorption, as typically associated with elastomers in the testing apparatus. FIG. 3B is a schematic diagram showing an example of gas flow for a fractured core sample 207B during the first-stage process 250 without gas leakage. In this case, any term in the equations above that contains a zero-value falls out. For example, if α=0 (no upstream leakage), then α can be disregarded in Eq. 5, and $α_{D0}$ would equal 0 in Eq. 9, which would then allow for all terms that contain $α_{D0}$ in Eqs. 20-23 to be disregarded as well. For an PDP experiment without any gas leakage (α=0, β=0), the normalized pressure difference across the core sample 107 is calculated by the simplified equation:

$$\ln(\Delta P_D) = \ln(P_{D1} - P_{D2}) \approx \ln(f_0) - \theta_1^2 t_D = \ln(f_0) - \theta_1^2 \frac{k_f}{c\mu\phi_f L^2} t, \quad (25)$$

where $f_0$ is a constant. The fracture permeability $k_f$ can be estimated through Eq. 25. The same equation can also be used for PDP experiments with gas leakage, but the estimated permeability would be the apparent fracture permeability $k_{af}$ without correction for gas leakage.

The log of the pressure difference (between the upstream reservoir 101 and downstream reservoir 103) is plotted. From the analytical solution, if the measurement system has no gas leakage, this curve is a straight line (see Eq. 25). The slope of this linear line can be used to estimate the matrix permeability. If there exists gas leakage in the system, however, the curve will bend down with the time measurement, or it will bend up if gas is desorbing from the instrument surfaces. For practical implementation, the first derivative of the log of this curve (that is, its slope) is calculated and plotted against time. A derivative line diverging from a constant-derivative line with time (for example, a straight line) can indicate the existence of gas leakage.

If gas leakage exists in the PDP experiment, the permeability estimates can be corrected to account for the leakage. By solving the physical model with gas leakage, the theoretical results for pressure difference between the upstream reservoir 101 and downstream reservoir 103 which are dependent on the gas leakage rates of the system and the permeability of the core sample 207A can be obtained. By matching the theoretical results for the pressure difference as a function of time with the experimental data, the permeability and the gas leakage rates can be determined simultaneously.

For instance, a permeability range ($k_1$, $k_2$) and gas leakage rate range ($α_1$, $α_2$) can be assigned. The analytical solutions for different permeability and gas leakage rate combinations within these ranges can be calculated, along with the squared difference between pressures from the analytical solution and the experimental data. The combination of permeability k and leakage rate a that provides the least squared difference, is the corrected estimate of the permeability and gas leakage rate, respectively. The pre-assigned gas leakage rate range can be determined from knowledge of the system.

The above analytical models can also be applied to the PDP experiment on an unfractured core sample 207A with single matrix permeability because the first-stage process 250 is substantially the same. The difference is that during the application, the fracture permeability $k_f$ is replaced with the matrix permeability $k_m$, and all the fracture-related parameters are replaced with matrix-related parameters. For instance, the dimensionless parameters a and b in Eq. 8 are converted to:

$$a = \frac{V_p}{V_1}, b = \frac{V_p}{V_2}, \quad (26)$$

where $V_p$ is pore volume of the unfractured core sample 207A. The simplification due to α or β (or both) being equal to zero is also the same for the first-stage process 250 of an unfractured core sample 207A.

After the first-stage process 250 is complete, the experiment for an unfractured core sample 207A is complete. For fractured core samples 207B, however, the first-stage process can provide the sample's fracture permeability, but further analysis of the second-stage process 270 can be completed to determine the sample's matrix permeability. Referring back to FIG. 2D, after the first-stage process 250 of a PDP experiment on a fracture core sample 207B, the gas flows from the void space (the sum of fracture, upstream reservoir 101, and downstream reservoir 103) into the matrix pores of the core sample 207B, resulting in a second pressure decline 209. This decay process is defined as the second-stage process 270. In the second-stage process 270, the upstream and downstream pressures are essentially equal. The pressure decline of the whole system can be modelled mathematically, and the analytical solution for the model can be used to determine core sample characteristics.

Figure 4A:
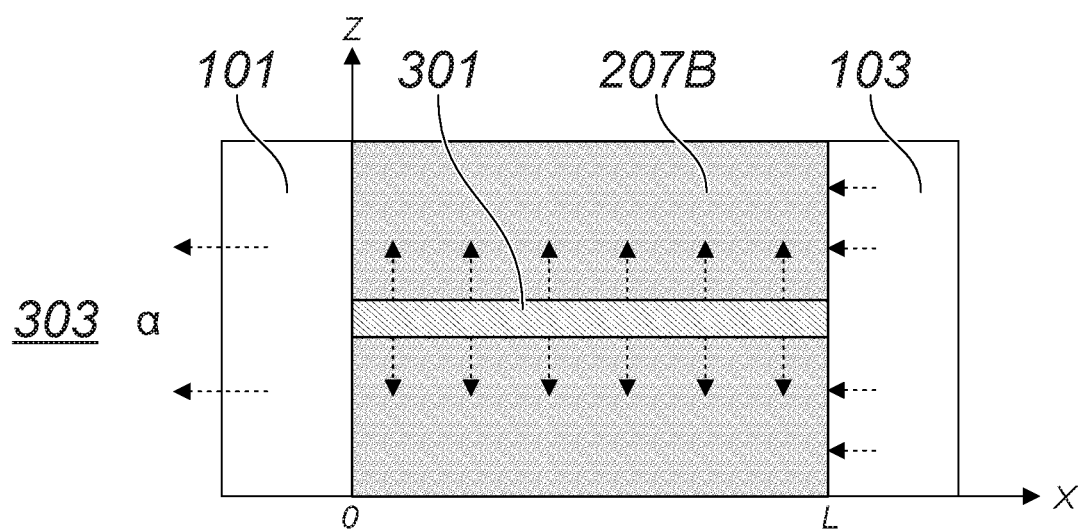
FIGS. 4A and 4B are simplified flow graphs of example 2nd-stage PDP experiments.
Figure 4B:
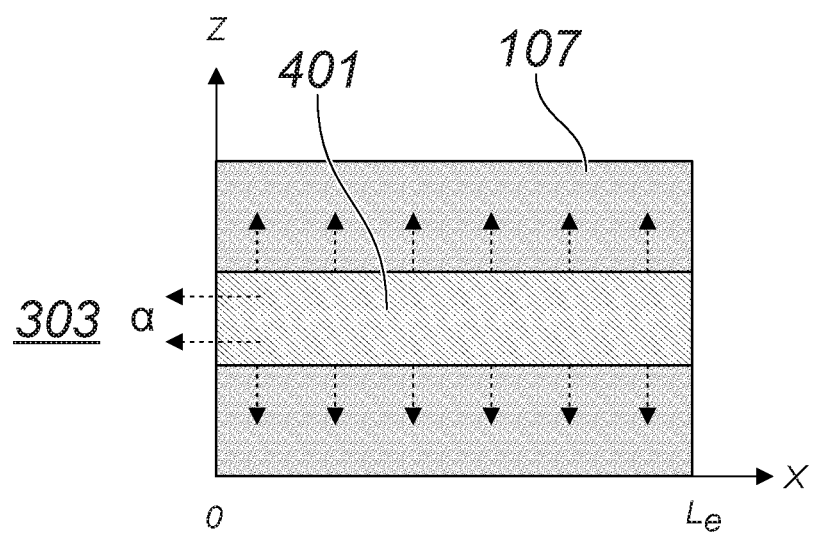

In order to establish a physical model to describe this second-stage process 270, the core sample 207B is approximated as a rectangular cube instead of a cylinder. FIG. 4A shows a two-dimensional gas flow model (along the x and z directions), and FIG. 4B shows a simplified one-dimensional gas flow model (along the z direction) for the second-stage process 270 with leakage rate a 303. In order to obtain the analytical solutions, some equivalent parameters are defined. The sum of upstream, downstream and fracture volume can be transformed to an equivalent volume $V_e$ 401 as:

$$V_e = V_1 + V_2 + V_f \quad (27)$$

The equivalent matrix height and matrix length are written as $$h_{me} = \frac{1}{\frac{1}{h_m} + \frac{1}{L}}, \quad (28)$$

$$L_e = h_m + L, \quad (29)$$

where $h_m$ is the rock matrix thickness. Since the upstream reservoir 101 and downstream reservoir 103 are connected through the fracture, we only need to assume one leakage rate, a 303.

Using Darcy's equation and the mass conservation equation, the differential equation for the pressure inside the core sample 207B, P(z,t), as a function of the distance z across the sample thickness and time t is calculated by:

$$\frac{\partial^2 P(z,t)}{\partial z^2} = \frac{c\mu\phi_m}{k_m} \frac{\partial P(z,t)}{\partial t}, 0 < z < h, t > t_1, h = \frac{h_{me}}{2}, \quad (30)$$

with the initial and boundary conditions:

$$P(z, t_1) = P_0(t_1), 0 < z < h, \quad (31)$$

-continued $$P(z, t_1) = P_1(t_1), z = h, \quad (32)$$

$$\frac{\partial P(z, t)}{\partial t} = -\frac{k_m}{c\mu} \frac{2dL}{V_e} \frac{\partial P(z, t)}{\partial z} - \alpha, t > t_1, z = h, \quad (33)$$

$$\frac{\partial P(z, t)}{\partial t} = 0, t > t_1, z = 0, \quad (34)$$

where $t_1$ the first-stage convergence time with gas leakage when the upstream pressure equals to the downstream pressure, and $\phi_m$ is the matrix porosity, excluding the fracture porosity, expressed as:

$$\phi_m = \frac{V_P}{V_b - V_f}. \quad (35)$$

The dimensionless gas leakage rate $\alpha_{D1}$ and dimensionless time $\tau_{D1}$ are defined as:

$$\alpha_{D1} = \frac{c\mu\phi_m h_{me}^2}{4k_m} \frac{1}{P_1(t_1) - P_2(0)} \alpha, \tau_{D1} = \frac{k_m}{c\mu\phi_m h^2}(t - t_1), \quad (36)$$

and $\omega$ is defined as:

$$\omega = \frac{V_P}{V_e} = \frac{2dL\phi_m h}{V_e}, \quad (37)$$

and $V_P$ is the volume of the matrix pores.

Through the Laplace transform and inverse Laplace transform, the exact solution for the normalized pressure of the upstream reservoir 101 and downstream reservoir 103 for the second-stage process 270 are given by:

$$U_{D1}(\tau_{D1}) = U_{D2}(\tau_{D1}) = \frac{P_1(t) - P_0(t_1)}{P_1(t_1) - P_0(t_1)} = C_3 + 2\sum_{n=1}^{\infty} e^{-\tau_{D1}\varphi_n^2}\left(\frac{1}{\omega + \frac{\varphi_n}{\omega} + 1} - \frac{\omega\alpha_{D1}}{\varphi_n^4 + \varphi_n^2 + \omega\varphi_n^2}\right) + \frac{\alpha_{D1} \times \tau_{D1}}{1 + \omega}, \quad (38)$$

where $C_3$ is a constant value which can be calculated by:

$$C_3 = 1 - 2\sum_{n=1}^{\infty}\left(\frac{1}{\omega + \frac{\varphi_n}{\omega} + 1} - \frac{\omega\alpha_{D1}}{\varphi_n^4 + \varphi_n^2 + \omega\varphi_n^2}\right), \quad (39)$$

and $\varphi_n$ are the roots of the following equation:

$$\tan(\varphi_n) = -\frac{\varphi_n}{\omega}, \varphi_n > 0, \quad (40)$$

Similar to the first-stage process, the leakage rate $\alpha$ 303 in the second-stage process can be zero for no gas leakage conditions. In this case, any term in the equations above that contains a zero-value rate falls out. In other words, in the case with no leakage, $\alpha$ can be disregarded in Eq. 33, and $\alpha_{D1}$ would equal 0 in Eq. 36, which would then allow for all terms that contain $\alpha_{D1}$ in Eqs. 38 and 39 to be disregarded as well. For the second-stage process 270 of a PDP experiment without any gas leakage ($\alpha=0$), the matrix permeability $k_m$ can be estimated by the following equation:

$$\ln\left(U_{D1} - \frac{1}{1 + \omega}\right) \approx \ln(f_1) - \varphi_1^2\tau_{D1} = \ln(f_1) - \varphi_1^2 \frac{k_m}{c\mu\phi_m L^2}(t - t_1), \quad (41)$$

where $f_1$ is a constant. The same equation can also be used for PDP experiments with gas leakage, but the estimated permeability would be the apparent matrix permeability $k_{am}$ without correction for gas leakage.

In order to detect whether gas leakage exists during the second-stage process 270, the log curve of the normalized transient pressure curve is plotted for the second-stage process 270. If there is no gas leakage with increasing time, this log curve is convergent to a straight line (see Eq. 41), and thus the slope of this line can be used to estimate the matrix permeability. If there exists gas leakage with increasing time, however, the log curve will bend down. For practical implementation, the first derivative of this log curve (that is, its slope) is plotted against time. A derivative line diverging from a constant-derivative line with time (for example, a straight line) can indicate the existence of gas leakage. Similar to analysis of the first-stage process, if gas leakage exists in the second-stage process of PDP experiment, the permeability estimate can be corrected to account for the leakage by matching the theoretical pressure decline with the experimental data.

The following transformations can be further applied to the equations above to find exact solutions. The Laplace transform is applied on $P_D$ in Eq. 42.

$$\widetilde{P_D}(x_D, s) = \int_0^\infty e^{-s^2 t_D} P_D(x_D, t_D) dt_D \quad (42)$$

By applying this transform, Eqs. 14, 18, and 19 can be converted to Eqs. 43, 44, and 45, respectively.

$$\frac{\partial^2 \widetilde{P_D}(x_D, t_D)}{\partial x_D^2} = s^2 \widetilde{P_D}(x_D, t_D), 0 < x_D < 1, t_D > 0, \quad (43)$$

$$a\frac{\partial \widetilde{P_D}(x_D, t_D)}{\partial x_D} = s^2 \widetilde{P_D}(x_D, t_D) - 1 - \frac{\alpha_{D0}}{s^2}, x_D = 0, \quad (44)$$

$$b\frac{\partial \widetilde{P_D}(x_D, t_D)}{\partial x_D} = -s^2 \widetilde{P_D}(x_D, t_D) + \frac{\beta_{D0}}{s^2}, x_D = 1, \quad (45)$$

Eq. 43 has the general solution:

$$\widetilde{P_D}(x_D, t_D) = A \sin h(sx_D) + B \cos h(sx_D), \quad (46)$$

where A and B are constant values that can be determined by the boundary conditions Eqs. 44 and 45.

By substituting Eq. 46 into Eqs. 44 and 45, A and B can be obtained by Eqs. 47 and 48, respectively.

$$A = \frac{-b(s^2 + \alpha_{D0})\sinh(s) - s(s^2 + \alpha_{D0})\cosh(s)}{s^2(bs^2\cosh(s) + abs\sinh(s) + s^3\sinh(s) + as^2\cosh(s))}, \quad (47)$$

$$B = \frac{(bs^2 + \alpha_{D0}b)\cosh(s) + s(s^2 + \alpha_{D0})\sinh(s) + \alpha\beta_{D0}}{s^2(bs^2\cosh(s) + abs\sinh(s) + s^3\sinh(s) + as^2\cosh(s))}. \quad (48)$$

Through the inverse Laplace transform, the dimensionless pressure $P_D$ is shown in Eq. 49.

$$P_D(x_D, t_D) = \frac{1}{2\pi i} \int_{-\infty i}^{+\infty i} e^{s^2 t_D} \widetilde{P_D}(x_D, s) ds^2 \qquad (49)$$

The complex integral, Eq. 49, can be solved by the Residue Theorem. Thus, the exact solutions for the dimensionless pressure in the upstream and downstream reservoirs can be expressed as shown in Eqs. 20-24 for the first-stage process of the PDP experiment. The same method can be applied to solve the differential equations, Eqs. 30-34, which are used to describe the second-stage process. The exact solution for the dimensionless pressure in the system can be expressed as shown in Eqs. 38-40 for the second-stage process of the PDP experiment.

Figure 5:
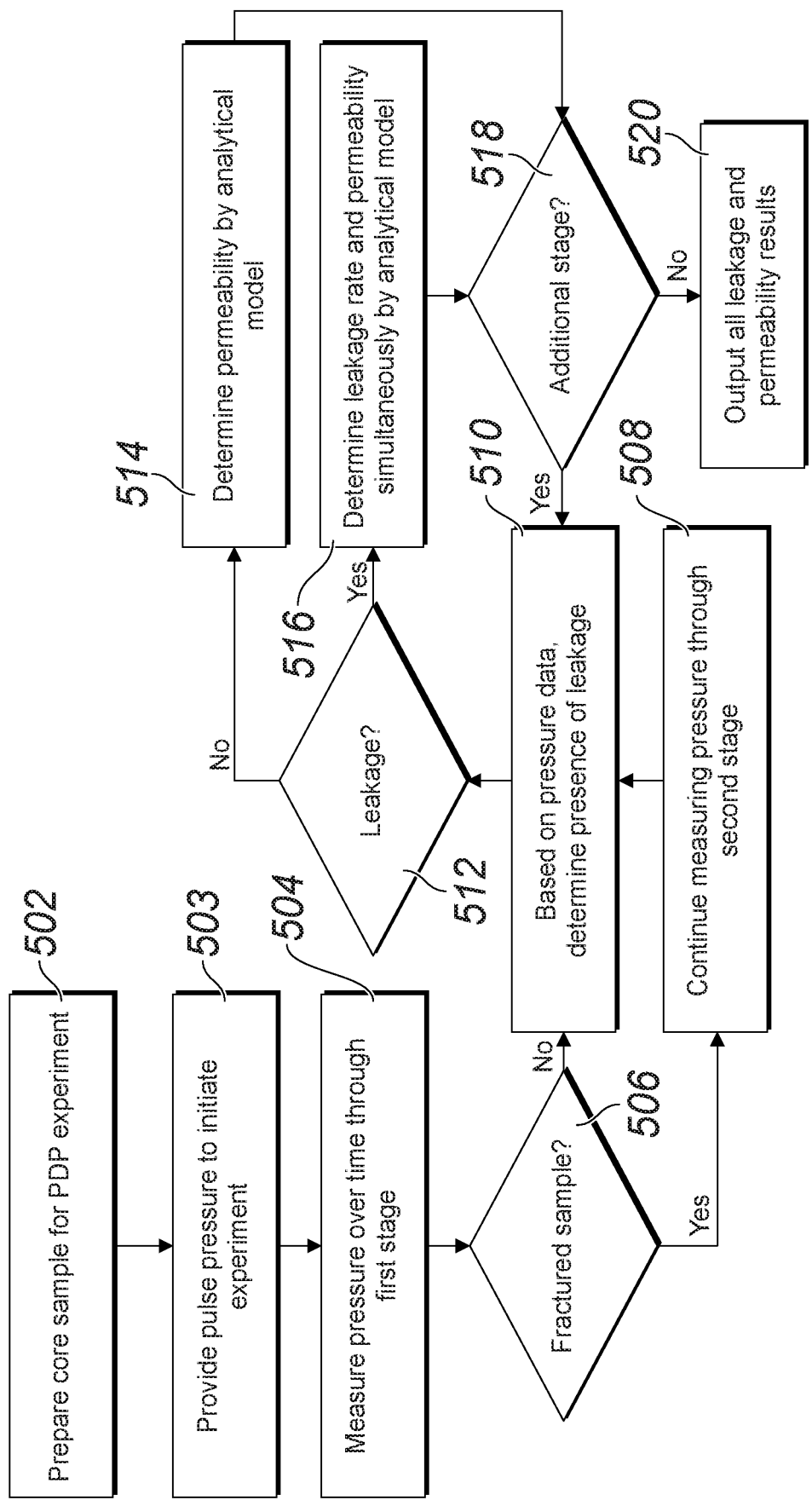
FIG. 5 is a flow chart illustrating an example method for a PDP experiment.

FIG. 5 shows a flowchart of an example method 500 for performing a PDP experiment on a core sample retrieved from a formation, according to an implementation. For clarity of presentation, the description that follows generally describes method 500 in the context of the other figures in this description. At 502, the core sample is prepared for the PDP experiment. For example, the preparation can comprise placing the core sample in the core holder of the testing apparatus. The preparation can further comprise supplying test gas to the upstream reservoir utilizing a pressure source, so that the initial pressure is high enough to diminish the Klinkenberg slipping effect—for example, 1,000 psig.

Once the upstream reservoir and downstream reservoir pressure has equalized, at 503, a pulse pressure is provided by the pressure source to initiate the PDP experiment. From 503, method 500 proceeds to 504, and transient pressure data of the upstream and downstream reservoirs are recorded over time through the first stage as fluid flows from the upstream reservoir to the downstream reservoir. At 506, if the sample is fractured, method 500 proceeds to 508, and transient pressure data of the system is recorded over time through the second stage. Method 500 then proceeds to 510. If the sample is unfractured, method 500 instead proceeds directly from 506 to 510, and the pressure data from the first-stage process is transformed to detect the presence or absence of gas leakage in the system. The transformation can comprise normalizing the pressure of the system, normalizing the pressure difference between the upstream and downstream reservoirs, calculating the logarithm of the normalized pressure curve, calculating the logarithm of the normalized pressure difference curve, or a combination of these. The presence of a leak can be determined by detection of a non-straight curve or deviation from a substantially straight line. The absence of a leak can be determined by detection of a straight (constant-slope) line.

If leakage is detected at 512, then the leakage rate and permeability is estimated at 516 by determining the combination of values that provide the best fit for the analytical model to the experimental data. If no leakage is detected at 512, then the permeability is estimated at 514 by applying the analytical model. If there was another stage in the PDP experiment (that is, second-stage process), then method 500 loops back to 510 for the additional stage. The permeability estimates obtained utilizing method 500 are corrected for any leakage that may exist in the testing apparatus.

Example 1

A PDP experiment of an implementation is simulated for a hypothetical unfractured core sample with various upstream leakage rate a. For an unfractured core sample, the PDP experiment comprises the first-stage process and determination of the sample's matrix permeability. The parameters of the unfractured core sample and the PDP system used in the simulation are provided in Table 1.

Unfractured Tight Core Sample and PDP Experiment Setup

TABLE 1

| Parameters | Value | Unit |
| --- | --- | --- |
| Core length | 1.5 | inch |
| Core width | 1 | inch |
| Matrix porosity | 7% | |
| Matrix permeability | $10^{-5}$ | millidarcy (mD) |
| Upstream volume (first-stage) | 1 | cubic centimeter (cc) |
| Downstream volume (first-stage) | 1 | cc |
| Initial pressure | 1,000 | psi |
| Pulse pressure | 40 | psi |
| Gas | Helium | |

Figure 6A:
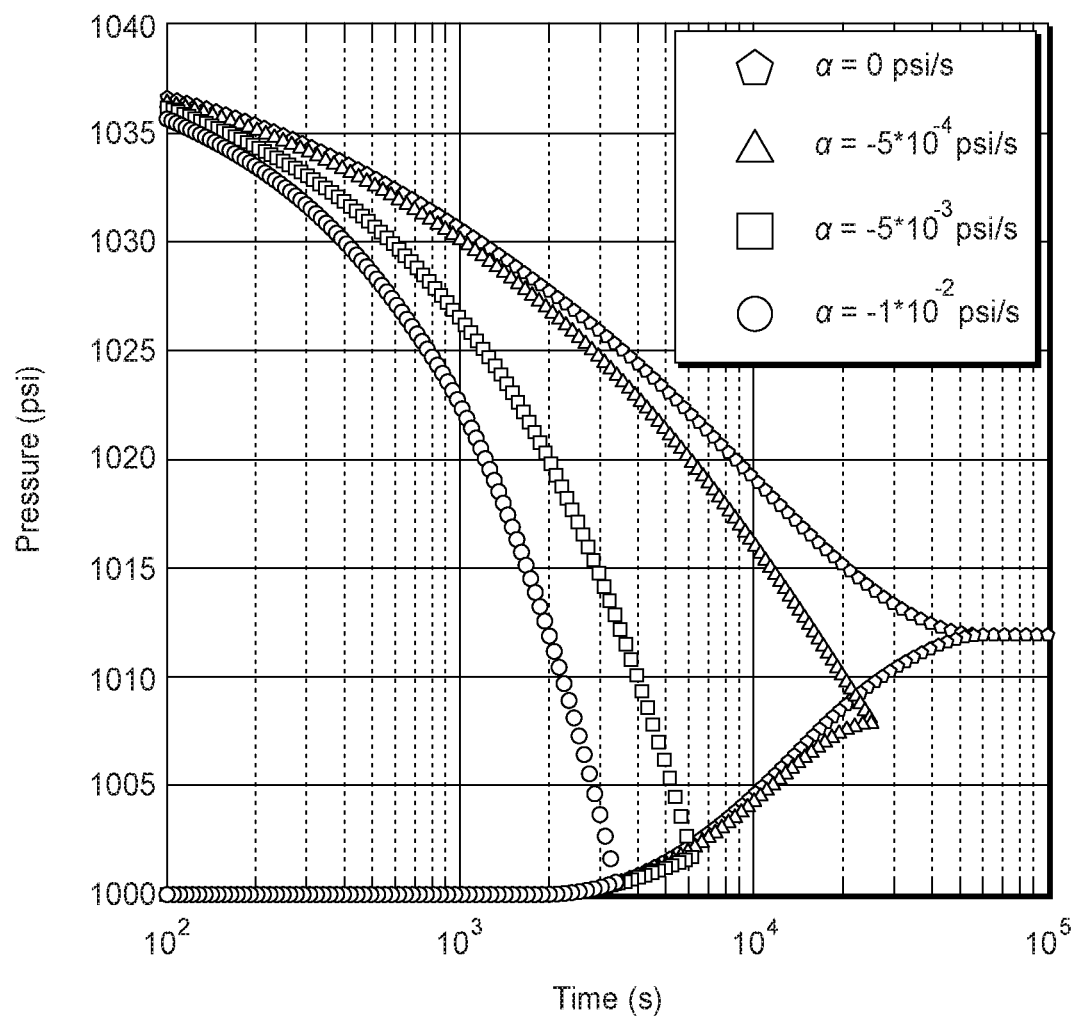
FIGS. 6A, 6B, 6C, and 6D are various data plots of an example PDP experiment.
Figure 6B:
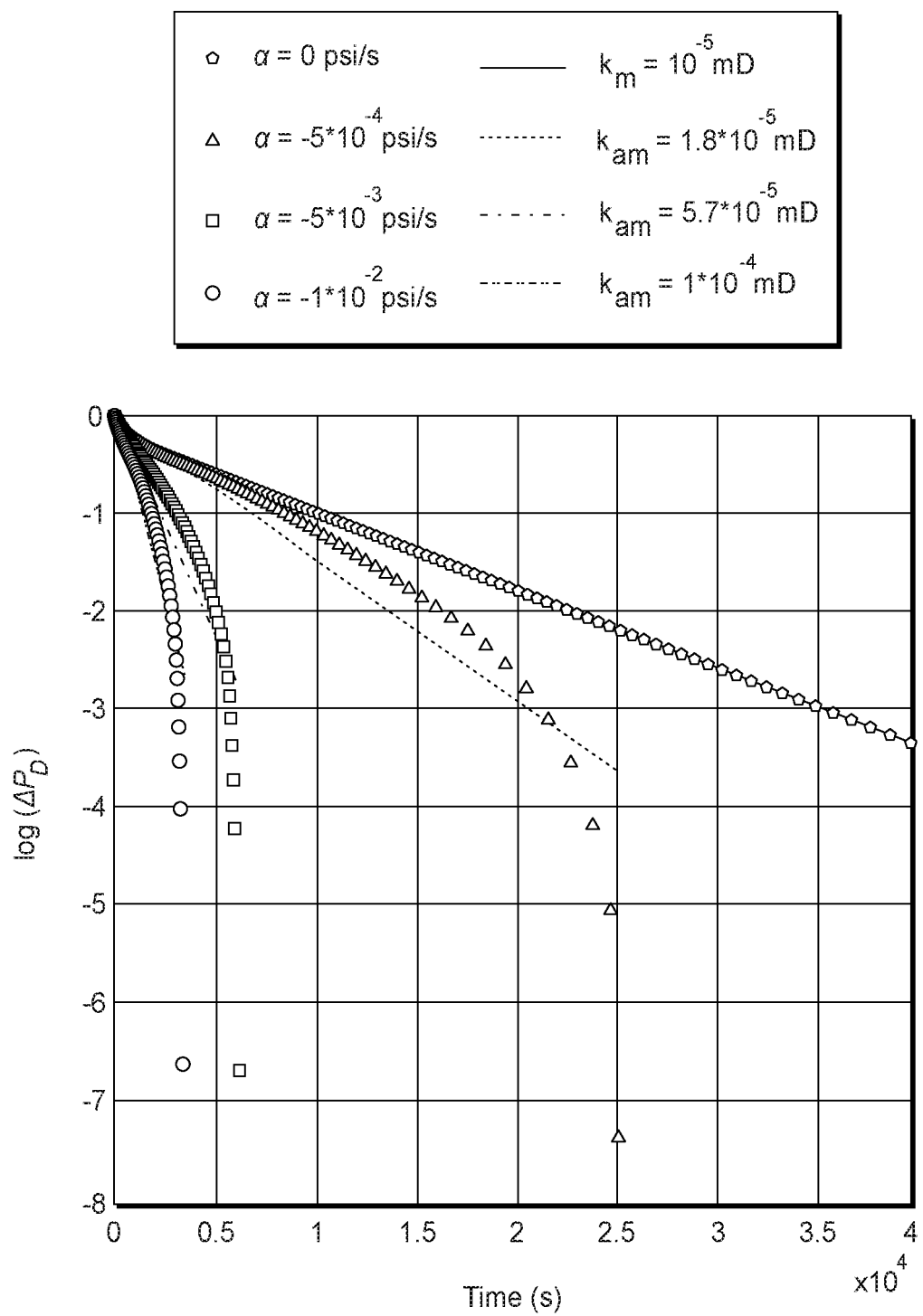
Figure 6C:
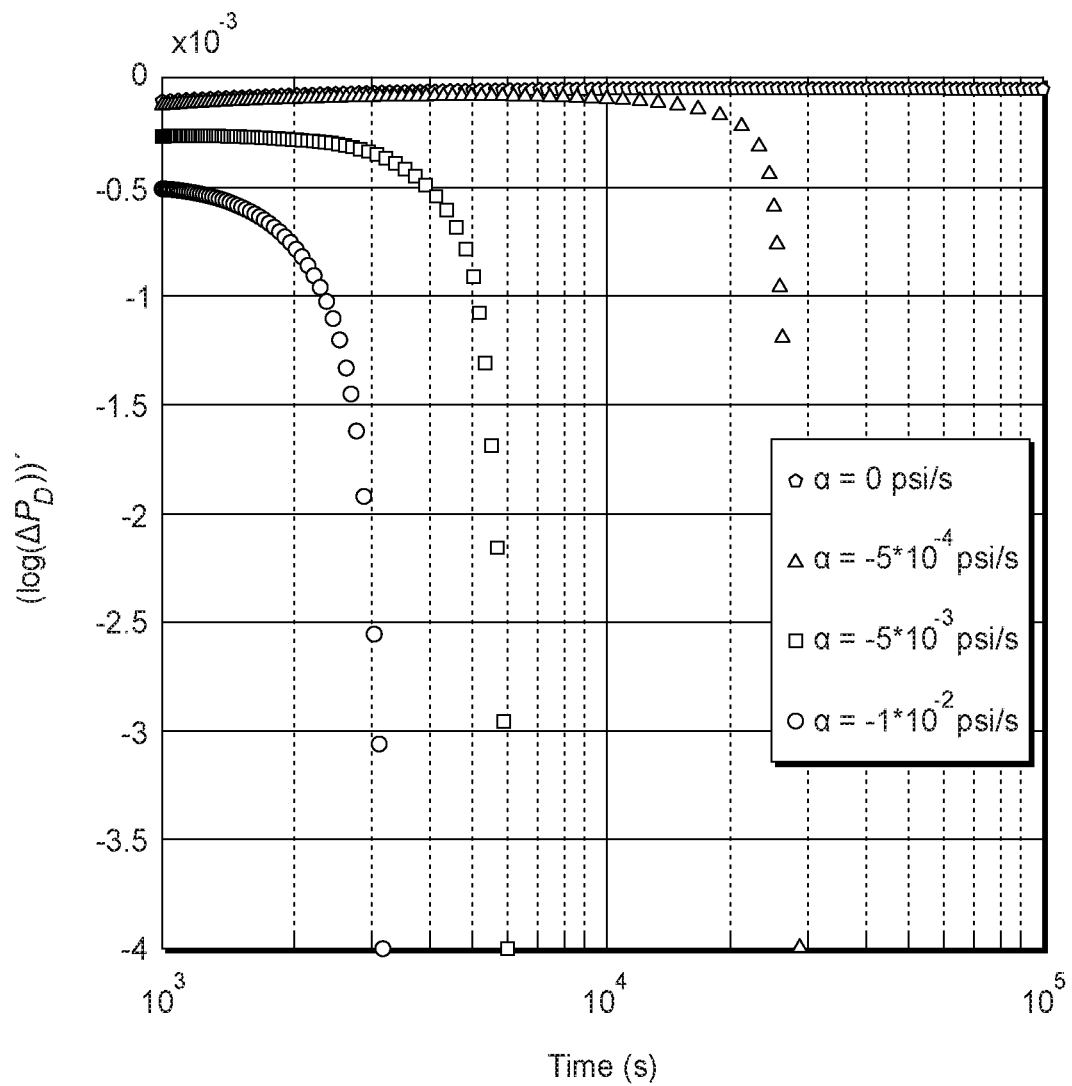

Gas leakage rates of 0 psi/s, $-5\times10^{-4}$ psi/s, $-5\times10^{-3}$ psi/s, and $-1\times10^{-2}$ psi/s were simulated for the same unfractured core sample. As shown in FIG. 6A, the leakage rate $\alpha$ affects the pressure transient curve of the upstream reservoir 101 and downstream reservoir 103. Increasing leakage rate can result in shorter convergence time, as well as a decrease in equilibrium pressure. FIG. 6B shows the logarithm of the normalized pressure difference ($\Delta P_D$) curve against time at various gas leakage rates, and FIG. 6C shows the first derivative (signified by an apostrophe) curves of the curves shown on FIG. 6B. In the case of no gas leakage ($\alpha$=0 psi/s), the logarithm of the normalized pressure difference curve and its first derivative curve are both straight lines. For non-zero gas leakage rates, the logarithm of the normalized pressure difference curve diverges from a linear line, and its first derivative curve also diverges from a constant value versus time. Eq. 25 is used to calculate the apparent matrix permeability at various gas leakage rates. FIG. 6B shows that as gas leakage rate increases, the larger the bias in estimating the matrix permeability, which is actually $10^{-5}$ mD as shown in the table.

Figure 6D:
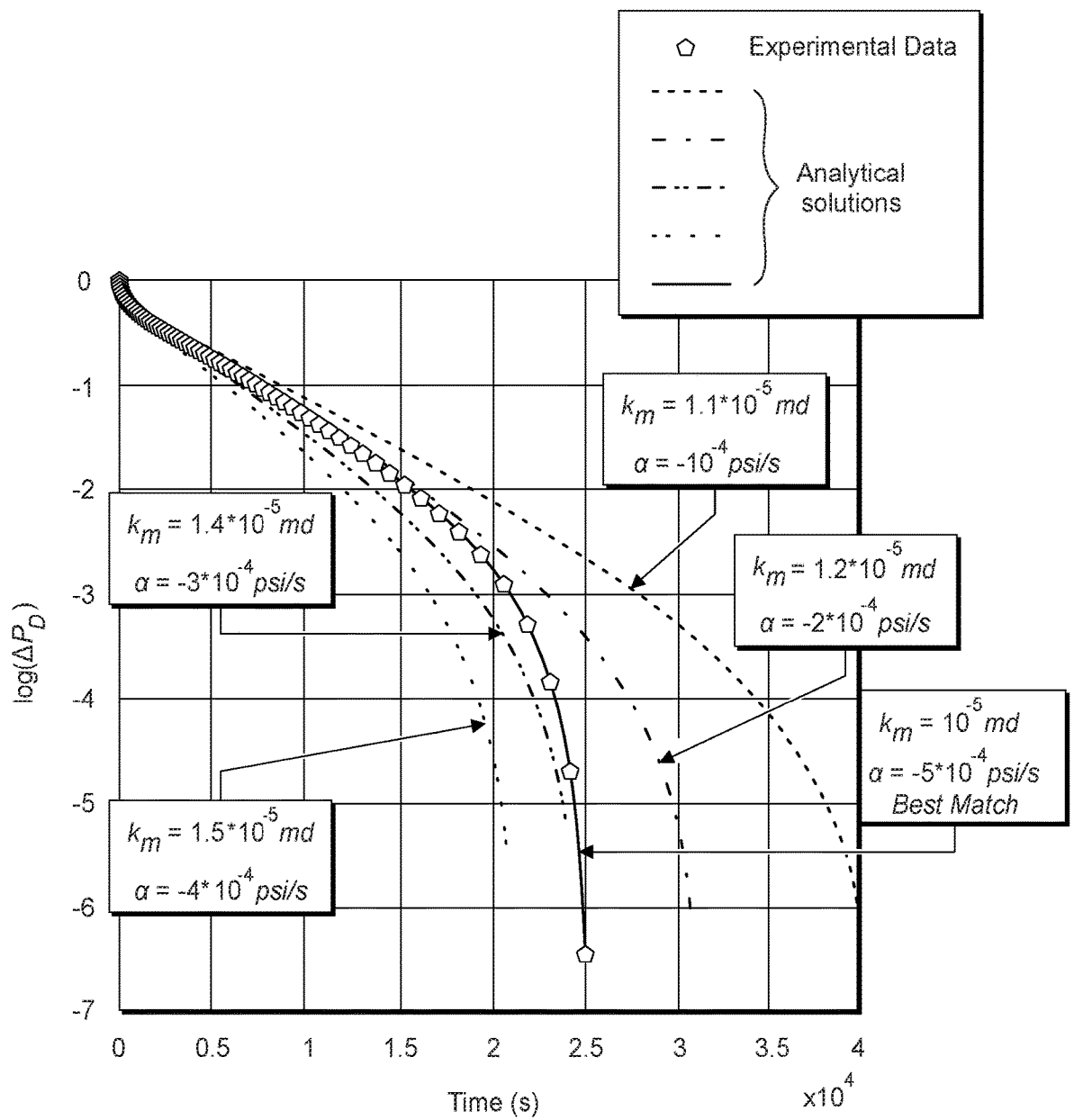

FIG. 6D shows a comparison of various analytical solutions of different matrix permeability and gas leakage rate combinations against the simulated measurement data. The logarithm of the normalized pressure difference ($\Delta P_D$) experimental data is plotted. Then, the analytical solutions for the log of the normalized pressure difference with various combinations of matrix permeability and gas leakage rate are calculated, and the analytical solution that best fits the experimental data provides the most accurate estimate of the sample's actual matrix permeability and the leakage rate of the system.

Example 2

A PDP experiment of an implementation is simulated for a hypothetical fractured core sample with various upstream leakage rate $\alpha$. For a fractured core sample, the PDP experiment comprises a first-stage process for determination of the sample's fracture permeability and a second-stage process for determination of the sample's matrix permeability. The physical model and leakage correction method for the first-stage process of a fractured sample are similar to those of an unfractured core sample (example above), but the permeability estimated is attributed to the fracture of the sample, instead of the matrix. The second-stage process of a fractured sample is then explored and analyzed to determine the impact of gas leakage on the estimation of matrix permeability. During the second-stage process, the pressures within the upstream reservoir, downstream reservoir, and the fracture of the sample are uniform. The parameters of the fractured core sample and the PDP system used in the simulation are provided in Table 2.

Fractured Tight Core Sample and PDP Experiment Setup

TABLE 2

| Parameters | Value | Unit |
| --- | --- | --- |
| Core length | 2 | inch |
| Core width | 1 | inch |
| Fracture porosity | 0.2% | |
| Matrix porosity | 7% | |
| Fracture permeability | 0.1 | mD |
| Matrix permeability | $10^{-5}$ | mD |
| Upstream/downstream volume (first-stage) | 30 | cc |
| Upstream/downstream volume (second-stage) | 1 | cc |
| Initial pressure | 1,000 | psi |
| Pulse pressure | 40 | psi |
| Gas | Helium | |

Figure 7A:
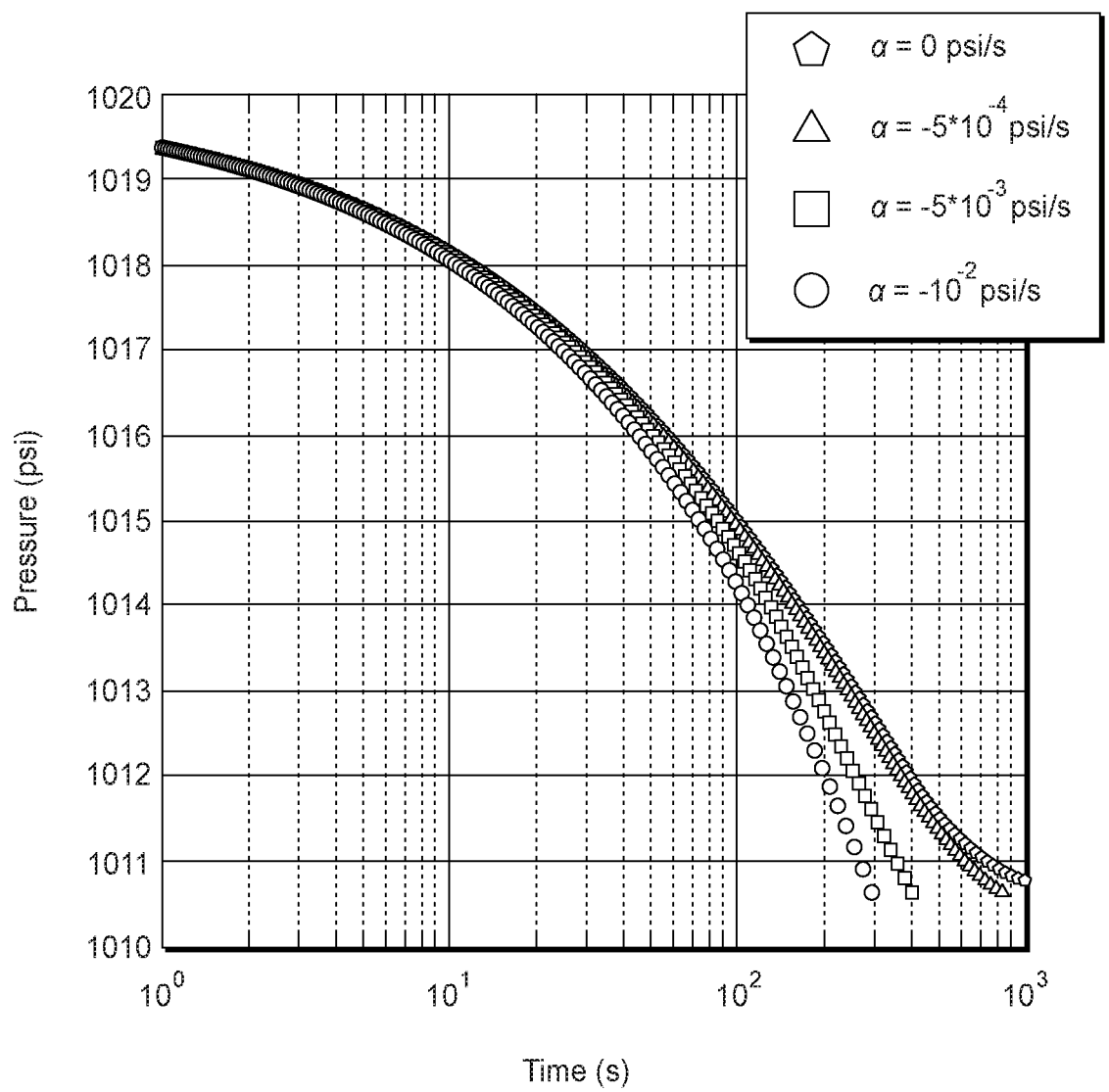
FIGS. 7A, 7B, 7C, and 7D are various data plots of an example PDP experiment.
Figure 7B:
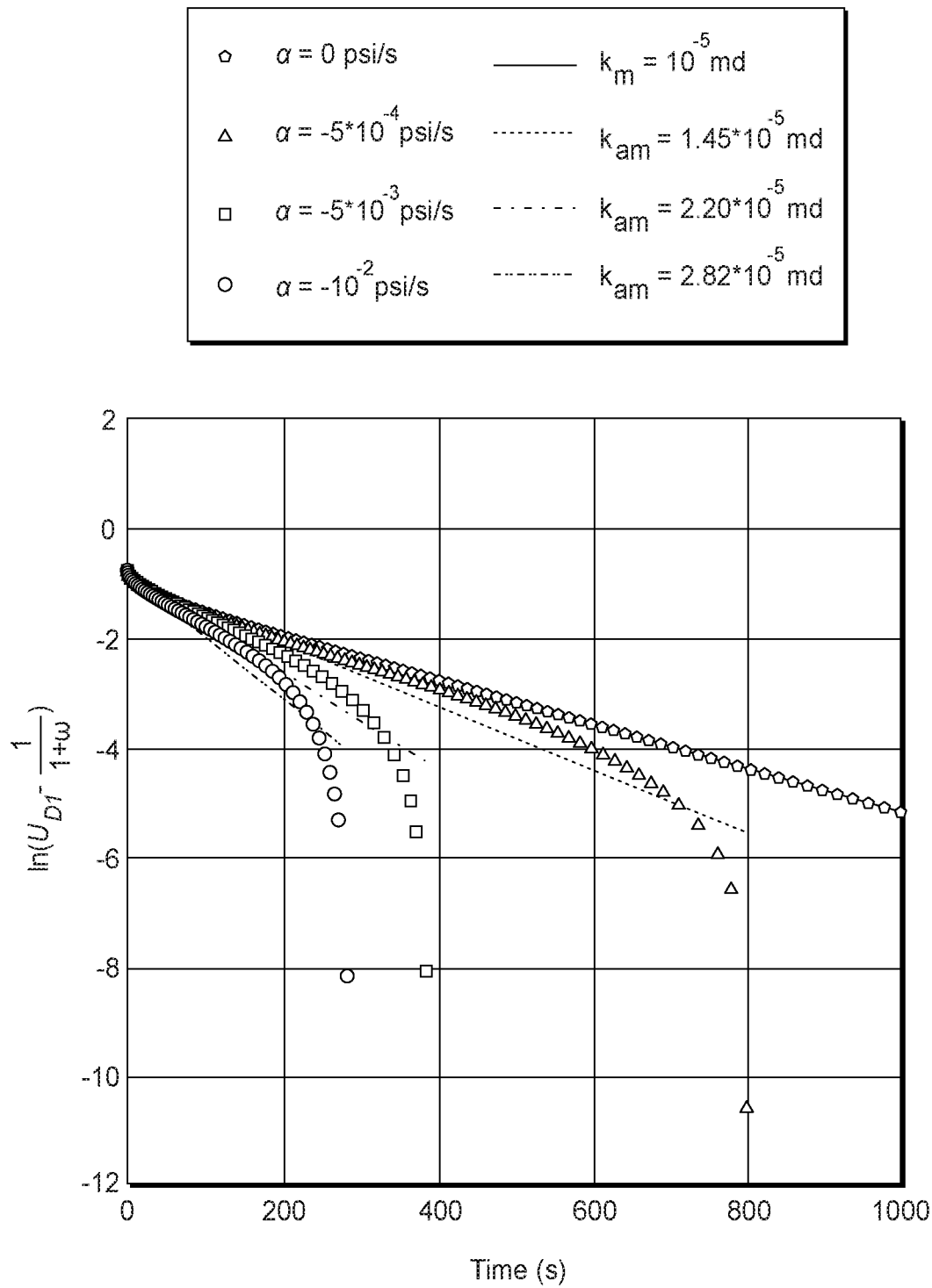
Figure 7C:
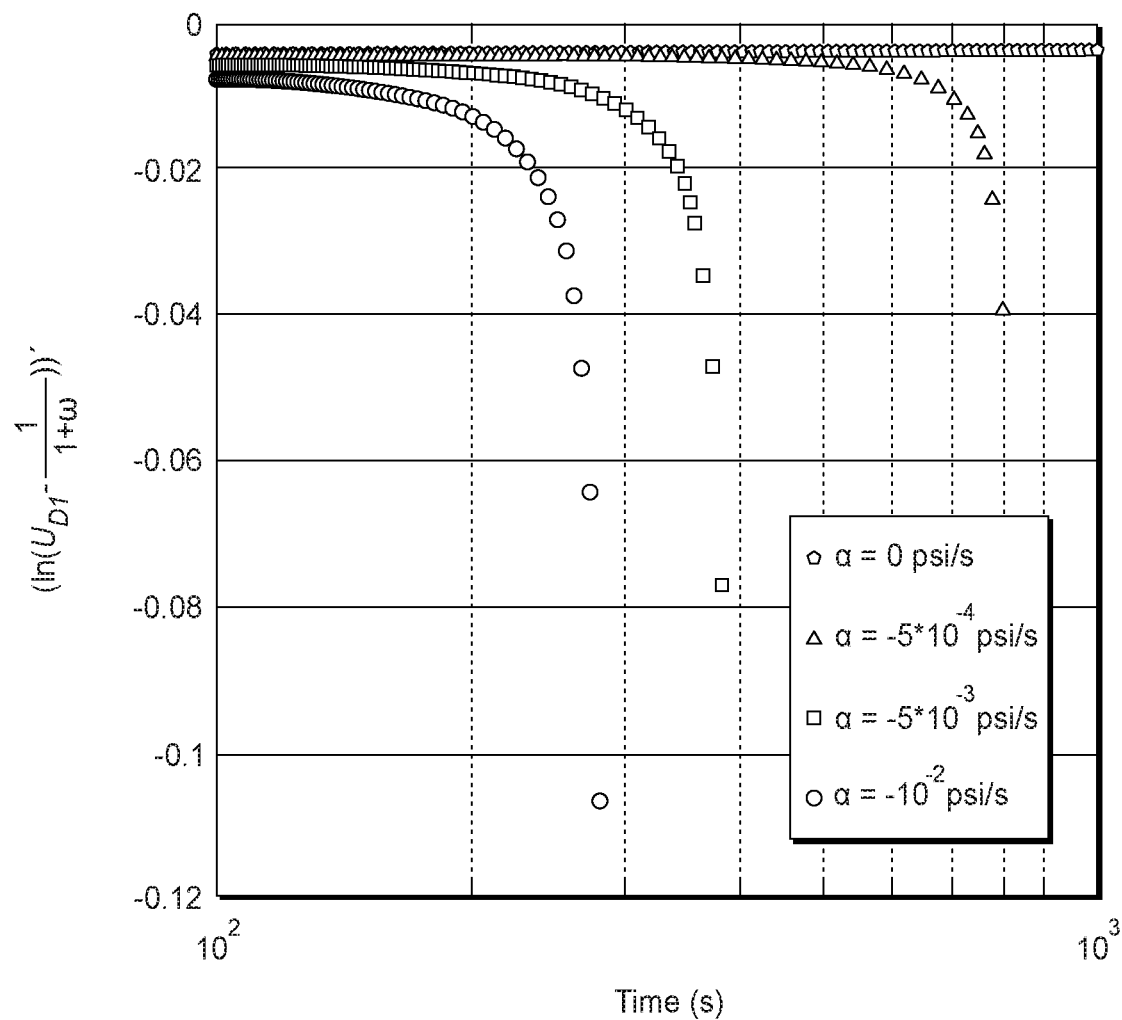

After finishing the first-stage process, the volume of the upstream and downstream reservoirs is reduced to 1 cc to enhance the pressure decay signal. Gas leakage rates of 0 psi/s, $-5 \times 10^{-4}$ psi/s, $-5 \times 10^{-3}$ psi/s, and $-1 \times 10^{-2}$ psi/s were simulated for the same fractured core sample. As shown in FIG. 7A, the leakage rate a affects the pressure transient curve: increasing leakage rate can result in faster pressure decay rate. FIG. 7B shows the logarithm of the normalized pressure transient curve against time at various gas leakage rates (refer to Eq. 41), and FIG. 7C shows the first derivative curves of the curves shown on FIG. 7B. In the case of no gas leakage ($\alpha=0$ psi/s), the logarithm of the normalized pressure transient curve and its first derivative curve are both straight lines. For non-zero gas leakage rates, the logarithm of the normalized pressure transient curve diverges from a linear line, and its first derivative curve also diverges from a constant value versus time. Eq. 41 is used to calculate the apparent matrix permeability at various gas leakage rates. FIG. 7B shows that as gas leakage rate increases, the larger the bias in estimating the matrix permeability, which is actually $10^{-5}$ mD as shown in the table.

Figure 7D:
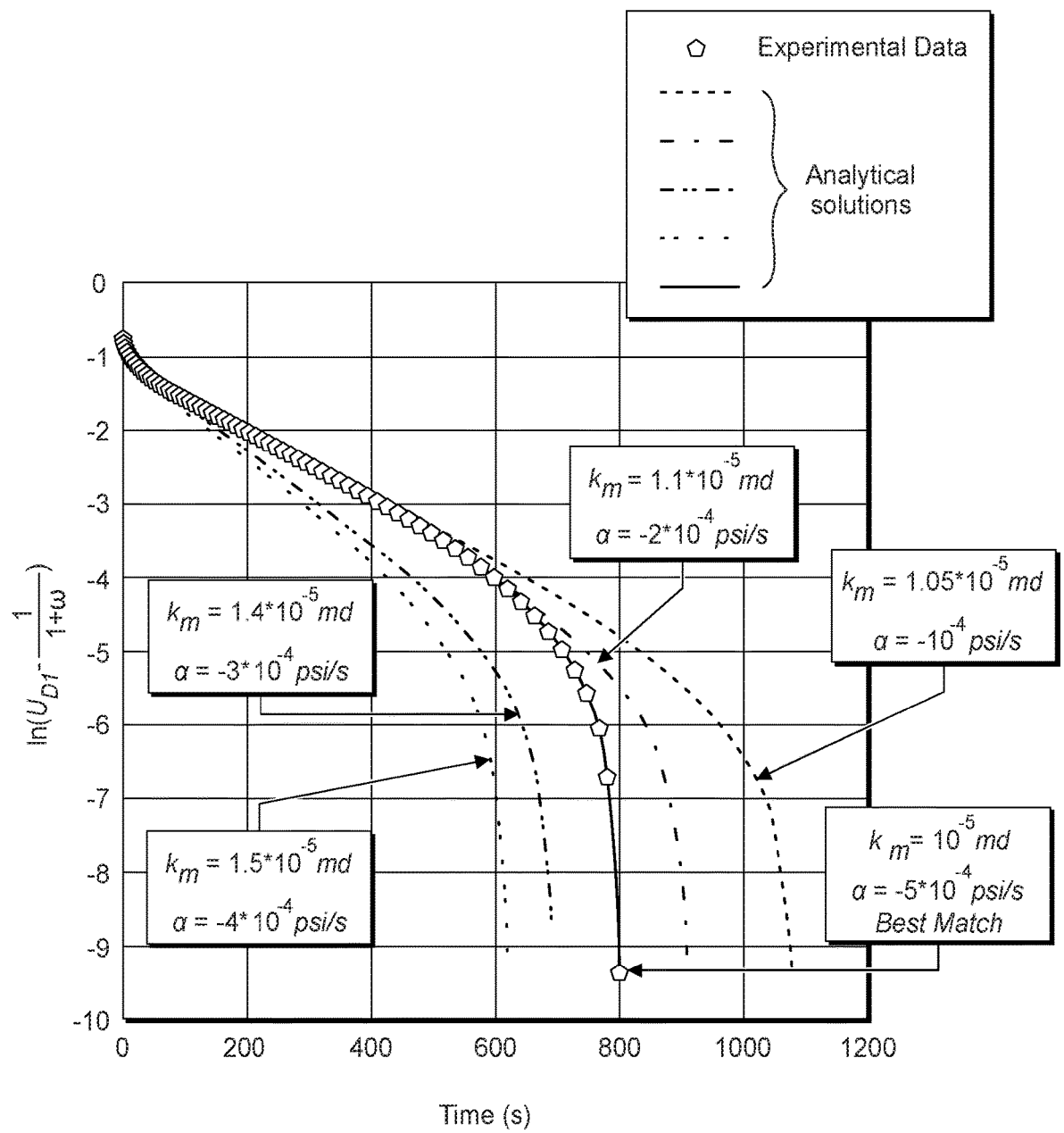

FIG. 7D shows a comparison of various analytical solutions of different matrix permeability and gas leakage rate combinations against the simulated measurement data. The logarithm of the normalized pressure experimental data is plotted. Then, the analytical solutions for the log of the normalized pressure with various combinations of matrix permeability and gas leakage rate are calculated, and the analytical solution that best fits the experimental data provides the most accurate estimate of the sample's actual matrix permeability and the leakage rate of the system.

Thus, certain implementations of the subject matter have been described. Other implementations are within the scope of the following claims.

What is claimed is:

1. A method comprising:
performing a pulse-decay permeability (PDP) experiment on a core sample retrieved from a formation, the PDP experiment comprising flowing fluid through the core sample in a sealed enclosure;
measuring, in response to flowing the fluid through the core sample, a change in fluid pressure over time;
determining, based on the change in fluid pressure over time, a presence or absence of leakage of fluid from the sealed enclosure; and
if the presence of leakage of fluid from the sealed enclosure is determined, determining a permeability of the core sample and a rate of leakage of fluid from the sealed enclosure simultaneously based on the change in fluid pressure over time, or
if the absence of leakage of fluid from the sealed enclosure is determined, determining a permeability of the core sample based on the change in fluid pressure over time.

2. The method of claim 1, wherein the permeability is determined by fitting a non-straight curve with consideration of the leakage effect.

3. The method of claim 1, wherein the sealed enclosure comprises an upstream reservoir, a downstream reservoir, and a core holder between the upstream reservoir and the downstream reservoir, wherein performing the PDP experiment on the core sample comprises:
positioning the core sample in the core holder; and
flowing the fluid into the upstream reservoir, through the core sample in the core holder, and into the downstream reservoir,
wherein the leakage of fluid from the upstream and downstream reservoirs is determined based on a pressure difference between an upstream reservoir and a downstream reservoir.

4. The method of claim 3, wherein the core sample is an unfractured core sample.

5. The method of claim 4, wherein measuring, in response to flowing the fluid through the unfractured core sample, the change in fluid pressure over time comprises recording pressure transient curves for each of the upstream and downstream reservoirs.

6. The method of claim 5, further comprising determining a log of an experimental pressure difference between the upstream and downstream reservoirs based on the pressure transient curves.

7. The method of claim 6, wherein determining the presence or absence of leakage of the fluid based on the change in fluid pressure over time comprises:
determining that the log of the experimental pressure difference is substantially a straight line; and
determining the absence of the leakage from the upstream and downstream reservoirs.

8. The method of claim 6, wherein determining the presence or absence of leakage of the fluid based on the change in fluid pressure over time comprises:
determining that the log of the experimental pressure difference is substantially a non-straight curve; and
determining the presence of the leakage from the upstream and downstream reservoirs.

9. The method of claim 8, wherein, in response to determining the presence of leakage of fluid from the upstream and downstream reservoirs, determining the leakage rate based on the change in fluid pressure over time comprises:
determining a theoretical pressure difference between the upstream and downstream reservoirs based on parameters of the fluid flowed through the unfractured core sample, the theoretical pressure difference being independent of the leakage from the sealed enclosure; and
comparing the theoretical pressure difference and the experimental pressure difference.

10. The method of claim 3, wherein the core sample is a fractured core sample comprising a fracture formed in a matrix of the core sample.

11. The method of claim 10, wherein measuring, in response to flowing the fluid through the fractured core sample, the change in fluid pressure over time comprises:
- measuring a first-stage change in fluid pressure over time, the first-stage change in fluid pressure based on flow of the fluid through the fracture;
- measuring a second-stage change in fluid pressure over time, the second-stage change in fluid pressure based on flow of the fluid through the matrix after the flow of the fluid through the fracture, and
- wherein determining, based on the change in fluid pressure over time, the presence of leakage of fluid from the sealed enclosure comprises determining that a log of the second-stage change in fluid pressure over time deviates from a substantially straight line.

\* \* \* \* \*